(12) United States Patent
Ulrich et al.

(10) Patent No.: US 7,716,069 B2
(45) Date of Patent: May 11, 2010

(54) SYSTEM AND METHOD FOR IMPLEMENTING MEDICAL RISK ALGORITHMS AT THE POINT OF CARE

(75) Inventors: Dennis A. Ulrich, London, KY (US); Burton E. Ulrich, Paducah, KY (US); Sandra I. Allen, Annville, KY (US)

(73) Assignee: Ulrich Medical Concepts Inc, Paducah, KY (US)

( * ) Notice: Subject to any disclaimer, the term of this patent is extended or adjusted under 35 U.S.C. 154(b) by 2282 days.

(21) Appl. No.: 10/406,162

(22) Filed: Apr. 3, 2003

(65) Prior Publication Data

US 2003/0191671 A1    Oct. 9, 2003

Related U.S. Application Data

(63) Continuation-in-part of application No. 10/207,739, filed on Jul. 27, 2002.

(60) Provisional application No. 60/310,412, filed on Aug. 6, 2001, provisional application No. 60/327,726, filed on Oct. 6, 2001.

(51) Int. Cl.
*G06Q 10/00* (2006.01)
*G06Q 50/00* (2006.01)
*G06Q 40/00* (2006.01)
*A61B 5/00* (2006.01)
*G06F 19/00* (2006.01)

(52) U.S. Cl. .................................. 705/3; 705/2; 705/4

(58) Field of Classification Search .................. 705/1, 705/2, 3, 4
See application file for complete search history.

(56) References Cited

U.S. PATENT DOCUMENTS

| | | | | |
|---|---|---|---|---|
| 5,235,510 | A * | 8/1993 | Yamada et al. | 600/300 |
| 5,471,382 | A * | 11/1995 | Tallman et al. | 600/300 |
| 5,772,585 | A | 6/1998 | Lavin et al. | |
| 5,807,256 | A * | 9/1998 | Taguchi et al. | 600/425 |
| 5,908,383 | A * | 6/1999 | Brynjestad | 600/300 |
| 6,022,315 | A * | 2/2000 | Iliff | 600/300 |
| 6,059,724 | A | 5/2000 | Campell et al. | |
| 6,063,026 | A | 5/2000 | Schauss et al. | |
| 6,110,109 | A | 8/2000 | Hu et al. | |
| 6,454,705 | B1 * | 9/2002 | Cosentino et al. | 600/300 |
| 6,482,156 | B2 * | 11/2002 | Iliff | 600/300 |

(Continued)

OTHER PUBLICATIONS

Dennis A. Ulrich, Forward by Dennis A. Ulrich, M.D., How to Use the Team Chart Concept, 2001, pp. vi-viii, Ulrich Medical Concepts, East Bernstadt KY.

*Primary Examiner*—Gerald J. O'Connor
*Assistant Examiner*—Amber L Altschul
(74) *Attorney, Agent, or Firm*—Stockwell & Smedley, PSC

(57) ABSTRACT

In a further aspect of the invention, the calculated results may be communicated as a graphical output 196, such as is illustrated in FIG. 27. The graphical output 196 may be accessed by pressing a graph report button 198 on the report output dialog box (FIG. 26). The graphical output 196 is useful to further illustrate to the physician and the patient the changes in the calculated risk value over time, and in relation to the cholesterol levels. The graphical output 196 is also useful as a further tool in enabling a patient to understand the relationship between their health habits and the associated risk factor, and in encouraging the patient to participate in their own medical decision making.

15 Claims, 27 Drawing Sheets

U.S. PATENT DOCUMENTS

| | | | |
|---|---|---|---|
| 2001/0012913 A1* | 8/2001 | Iliff .......................... 600/300 |
| 2001/0029322 A1* | 10/2001 | Iliff .......................... 600/300 |
| 2001/0051787 A1* | 12/2001 | Haller et al. ................. 604/66 |
| 2002/0013613 A1* | 1/2002 | Haller et al. ................. 607/60 |
| 2002/0035486 A1* | 3/2002 | Huyn et al. ..................... 705/3 |
| 2002/0038227 A1* | 3/2002 | Fey et al. ...................... 705/3 |
| 2002/0052761 A1* | 5/2002 | Fey et al. ...................... 705/2 |
| 2002/0077865 A1* | 6/2002 | Sullivan ........................ 705/3 |

* cited by examiner

20

Add New Contact

Last Name [Patient]   First Name [Paula]
Company [ ]
Please check the appropriate box if this contact is a...
☑ Patient
☐ Pharmacy
☐ Physician or Health Care Provider
    ☐ Include Physician Quick Access List
    Unique Physician ID Number (UPIN) [ ]
    Signature Line Text (HCFA 1500 Box 31) [ ]
☐ Insurance Company
    Electronic Billing Defaults (EMC NSF 301)
    AAO 17 0 Receiver ID [ ]
    AAO 18 0 Organization Type [ ▼]
    CAO 23 0 Claim Edition Indicator [ ▼]
    DAO 05 0 Source of Payment [ ▼]

You must enter a last name or a company name.   [OK] [Cancel]

| PATIENT REGISTRATION | | | | | | X |
|---|---|---|---|---|---|---|
| LAST NAME Doe | FIRST Jane | MIDDLE | | [X] PATIENT | | |
| SSN 111 22 3333 | DATE OF BIRTH | | SEX F | | | |

ADDRESS: 100 Main Street
ADDRESS:
ADDRESS:
CITY: Any City   STATE: KY   ZIP: 40000

PHONES
HOME
WORK
EMERG

EMPLOYER [CLEAR] FEE SCHEDULE [MEDICARE FEE SCHEDULE] [CLEAR]

☐ SINGLE  ☐ EMPLOYED  ☐ MARRIED  ☐ FULL TIME STUDENT  ☐ PART TIME STUDENT  ☐ OTHER

CURRENT PROBLEMS [ADD] [DEL]
Adjustment Reaction
Constipation
Stiffness

ALLERGIES [ADD] [DEL]
Augmentin
CIPRO
PCN

MEDICATIONS [ADD] [DEL]
ACIPHEX
AMARYL
Atrovent Inhaler

PRIMARY INSURANCE
1ST INS [CLEAR]
INSURED [CLEAR]
PATIENT RELATIONSHIP TO INSURED
○ SELF ○ SPOUSE ○ CHILD ○ OTHER
PLAN/PROGRAM Unisys
GROUP #
INSURED ID # 1000000 00B
CO-PAY $ 0.00   %   DEDUCT $ 0.00
⦿ MEDICARE  ○ CHAMPUS  ○ GROUP  ○ OTHER
○ MEDICAID  ○ CHAMPVA  ○ FECA BLACK LUNG

SECONDARY INSURANCE
2ND INS [CLEAR]
INSURED [CLEAR]
PATIENT RELATIONSHIP TO INSURED
☐ SELF ☐ SPOUSE ☐ CHILD ☐ OTHER
PLAN/PROGRAM
GROUP #
INSURED ID #
CO-PAY $   %   DEDUCT $
NEVER RECEIVES A STATEMENT
STATEMENT ONLY IF INS FAILS TO PAY   [OK] [CANCEL]

SEARCH DIAGNOSIS DICTIONARY　　　X

Query Key　　　　　　　　　　　　　Query On　[Code ▼]

[　　　　　　] [Query]　　　　　　Sort By　[Description ▼]

[Select] [Exhaustive Research] [Display Commonly Used Codes] [Print All]

[Add] [Edit] [Delete] [Print Entry] [Print List] [List to File] [Records to File] [Cancel]

List　☐ Show Deleted Items　☐ Show Comments　Entries [724]

| | |
|---|---|
| Abdominal aneurysm without mention of rupture | 441.4 |
| Abdominal pain A | 789.2 |
| Abdominal pain B | 341.4 |
| Abdominal pain C | 654.7 |
| Abdominal pain D | 556.3 |
| Abdominal pain E | 541.7 |
| Abdominal pain F | 782.6 |
| Abdominal pain G | 740.4 |
| Abdominal pain H | 679.2 |

SEARCH PROCEDURE DICTIONARY     X

Query Key     Query On [Description ▼]

[ Query ]    Sort By [Description ▼]

| Select | Exhaustive Research | Display Commonly Used Codes | Print All |

| Add | Edit | Delete | Print Entry | Print List | List to File | Records to File | Cancel |

List   ☐ Show Deleted Items   ☐ Show Comments    Entries   724

| | |
|---|---|
| Ace Wrap | 4414 |
| Ampicilin | 7892 |
| CXR | 3414 |
| Arthritis Panel | 6547 |
| B12 Injection | 5563 |
| Culture Chlamidia | 5417 |
| Depo Prevara | 7826 |
| CBC | 7404 |
| Procedure X | 6792 |

CARE PLAN REMINDER DEFINITION — 162

| Field | Value |
|---|---|
| Description | Select a New Mammogram Program |
| Timeline Category | Care Plan |
| Lead Time | 5 YEARS ▶ |
| Repeat Count | (How Many Additional Reminders?) ▶ |
| Repeat Interval | |
| Comments | 5 Years have gone by since your original mammogram care plan was decided upon and implemented. You probably want to reevaluate the patient's condition and choose an appropriate care plan. |

[OK] [Cancel]

FIG. 22

DEFINE USER TIMELINE RECORD

A COMPUTED USER DEFINED FIELD IS NOT ENTERED BY THE USER. THE VALUE ASSIGNED TO A USER DEFINED FIELD IS COMPUTED BASED ON THE VALUES OF OTHER USER DEFINED FIELDS.
A VALUE CAN BE CONDITIONALLY ASSIGNED THAT IS A CERTAIN CONDITION MUST BE TRUE FOR A CERTAIN VALUE TO BE ASSIGNED. USE THE DIALOG BOX TO SPECIFY THOSE VALUES AND OPTIONAL CONDITIONS.
THE ORDER WHICH CONDITION/VALUE ENTRIES ARE DEFINED HERE IS THE ORDER IN WHICH CONDITIONS WILL BE EVALUATED AT RUN-TIME. IF THE "COMBINED VALUES" CHECK BOX IS CHECKED, THEN THE RUN-TIME VALUE ASSIGNED TO THIS FIELD WILL BE THE COMBINATION OF ALL VALUES LISTED HERE WHOSE CORRESPONDING EVALUATE IS TRUE (AT RUN-TIME).

FIELD NAME [        ]                                      ☐ COMBINED VALUES

IF ([TOTT FRF] = 17 AND PATIENT -> SEX="M") THEN 30
IF ([TOTT FRF] = 16 AND PATIENT -> SEX="M") THEN 25
IF ([TOTT FRF] = 15 AND PATIENT -> SEX="M") THEN 20
IF ([TOTT FRF] = 14 AND PATIENT -> SEX="M") THEN 16
IF ([TOTT FRF] = 13 AND PATIENT -> SEX="M") THEN 12
IF ([TOTT FRF] = 12 AND PATIENT -> SEX="M") THEN 10
IF ([TOTT FRF] = 11 AND PATIENT -> SEX="M") THEN 8
IF ([TOTT FRF] = 10 AND PATIENT -> SEX="M") THEN 6
IF ([TOTT FRF] = 9 AND PATIENT -> SEX="M") THEN 5
IF ([TOTT FRF] = 8 AND PATIENT -> SEX="M") THEN 4
IF ([TOTT FRF] = 7 AND PATIENT -> SEX="M") THEN 3
IF ([TOTT FRF] = 6 AND PATIENT -> SEX="M") THEN 3
IF ([TOTT FRF] = 5 AND PATIENT -> SEX="M") THEN 2
IF ([TOTT FRF] = 4 AND PATIENT -> SEX="M") THEN 2
IF ([TOTT FRF] = 3 AND PATIENT -> SEX="M") THEN 1
IF ([TOTT FRF] = 2 AND PATIENT -> SEX="M") THEN 1

COMMENTS

| ADD CONDITION/VALUE | COPY/PASTE | EDIT | ORDER | DELETE | CLEAR ALL |

CANCEL

FIG. 26

Ulrich Medical Clinic - Lipids by Patient, For: Test, Jack (05-16-2000 to 03-28-2003 (Stated))
Report Run on 03-28-2003 Fri 02:12:19 PM

| Date | TRG | Tch | LDL | HDL | VLDL | FRS % 10 yr risk |
|---|---|---|---|---|---|---|
| 2000-11-02 | 213 | 298 | | 34 | | 16 |
| 2000-12-04 | 321 | 312 | 156 | 34 | | 30 |
| 2001-04-17 | 200 | 175 | 130 | 45 | | 30 |
| 2001-08-30 | 360 | 260 | | 45 | | 5 |
| 2002-04-06 | 321 | 123 | 321 | 39 | 32 | 30 |
| 2002-04-06 | 345 | 234 | | 12 | | 25 |
| 2002-04-06 | 360 | 256 | 165 | 16 | | |
| 2002-04-18 | 256 | 245 | 167 | 60 | 34 | |
| 2002-06-28 | 234 | 321 | 167 | 23 | 23 | |
| 2002-10-19 | 231 | 245 | 197 | 34 | 12 | |

End of Report.

SYSTEM AND METHOD FOR IMPLEMENTING MEDICAL RISK ALGORITHMS AT THE POINT OF CARE

CROSS REFERENCE TO RELATED APPLICATIONS

This application is a continuation in part of U.S. application Ser. No. 10/207,739, filed Jul. 27, 2002, which claims the benefit of U.S. Provisional Application Ser. No. 60/310,410, filed Aug. 6, 2001 and U.S. Provisional Application Ser. No. 60/327,726, filed Oct. 6, 2001, the contents of which are incorporated herein by reference.

AUTHORIZATION UNDER 37 CFR SEC. 1.71

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all rights whatsoever.

BACKGROUND OF THE INVENTION

1. Field of the Invention

The present invention relates generally to a system and method for estimating and tracking a patient's risk for various medical conditions and, in particular, to a system and method for estimating and tracking a patient's risk for various medical conditions using an electronic medical records system.

2. Related Prior Art

A goal of medical research is to identify diagnostic measurements useful in revealing present of forecasting future disease states. In few cases, a disease state is revealed from a single diagnostic measurement. More often, a disease state can be detected with more sensitivity through recognizing the subtle relationship between two or more diagnostic measurements and a disease state.

The relationships between disease states and diagnostic measurements are frequently published in medical journals. These journals report medical algorithms, which are formulae by which the likelihood of a disease state can be computed by entering data from diagnostic measurements. Reliance on medical algorithms by medical practioners can reduce the number of medical errors, and efficiently promote the well being of patients.

Despite the great number of useful medical algorithms available, most practitioners use only a small number of them routinely. A major barrier preventing their application in practice is the lack of a convenient system for using the algorithms at the point of care. Compounding this barrier, both patient data and medical algorithms change over time as new information comes available. It is commonly known that health care providers, such as physicians, produce large volumes of diagnostic data which must be utilized in order to service patients. Constantly updating patients' diagnostic and/or risk assessment is unduly burdensome in view of these changes. Algorithms would be more widely utilized if clinicians could readily integrate them into a system that included patient data.

Electronic medical records systems have been developed in an attempt to insure accurate and complete input of information, and to facilitate information processing, retrieval and reporting. These electronic record systems are intended to ultimately replace patient records maintained in paper files, and generally attempt to reduce the workload of medical personnel in processing the information contained in these records.

Although various advantages have been provided by electronic medical records systems currently available, there is a continuing need for a relational data base model which provides a means for the rapid incorporation of diagnostic data into medical algorithms. Further, there is a need for such a relational data base model which provides a means for updating medical algorithms as they are published in medical journals. Further, there is a need for such a system, which will allow these modifications without requiring major software upgrades.

SUMMARY OF THE INVENTION

The present invention provides medical practitioners with a convenient interface through which practitioners can incorporate patient data into medical algorithms, allowing the rapid assessment of a patient's disease state or risk of disease state at the point of care. The central computer acts to store a database of diagnostic data and medical algorithms allowing the practioners to assess the risk of a disease state from the diagnostic information. Optionally, the invention also stores other information relating to a medical practice, including patient records, stored information for implementation into patient records, such as patient care plans, billing, payment and scheduling records, as well as any other records required for operation of the medical facility. The system generally includes information previously contained in paper documents, including patient charts, business related contact information and information required to facilitate tracking of patients and their medical progress. Additionally, the present system may facilitate compliance with third party insurance provider requirements, such as Medicare, and in particular, facilitates selection of information for claim forms in order to insure an optimum financial return through selection of appropriate procedure codes for a patient encounter.

In one aspect of the invention, a method of managing a patient encounter using an electronic medical records system is provided, the method including collecting and storing individual patient medical information in specified fields on a computer, providing a calculated field, the calculated field including a value calculated from information in at least one of the specified fields, and the calculated field providing an indication to a user of a health risk associated with the information in the specified fields.

In another aspect of the invention, a method of assessing a patients risk of a disease state is provided, including collecting and storing individual patient medical diagnostic information on a computer, collecting and storing a medical algorithm that operates on the medical diagnostic information to generate a disease risk assessment, applying the algorithm to the diagnostic data of one or more patients to generate one or more risk assessment values and generating a report to communicate the risk assessment values to a patient or medical practitioner.

Other objects and advantages of the invention will be apparent from the following description, the accompanying drawings and the appended claims.

BRIEF DESCRIPTION OF THE DRAWINGS

FIG. 3 illustrates a new contact dialog box for the system;

FIG. 5 illustrates the dialog box of FIG. 4 with a demographics tab selected;

FIG. 6 illustrates the dialog box of FIG. 4 with a timeline tab selected;

FIG. 7 illustrates a patient registration dialog box for the system;

FIG. 9 illustrates the dialog box of FIG. 8 with an encounters tab selected;

FIG. 14 illustrates a dialog box for accessing a dictionary containing diagnosis codes for inclusion in an encounter;

FIG. 15 illustrates a dialog box listing procedures for inclusion in an encounter;

FIG. 17 illustrates a dialog box for editing a procedure entry;

FIG. 20 illustrates the dialog box of FIG. 19 with a further reminder for inclusion in the care plan of the dialog box of FIG. 18;

FIG. 22 illustrates a dialog box for defining a computed user defined field for the user defined record;

FIG. 26 illustrates a dialog box for providing a report output and including values from the computed user defined record.

DETAILED DESCRIPTION OF THE INVENTION

The present invention provides a method and system for electronically maintaining medical records and is particularly designed to eliminate the need for paper records, such as paper medical charts, and to facilitate availability and use of information relating to patients, as well as other information used in the operation of a medical facility.

Figure 1:
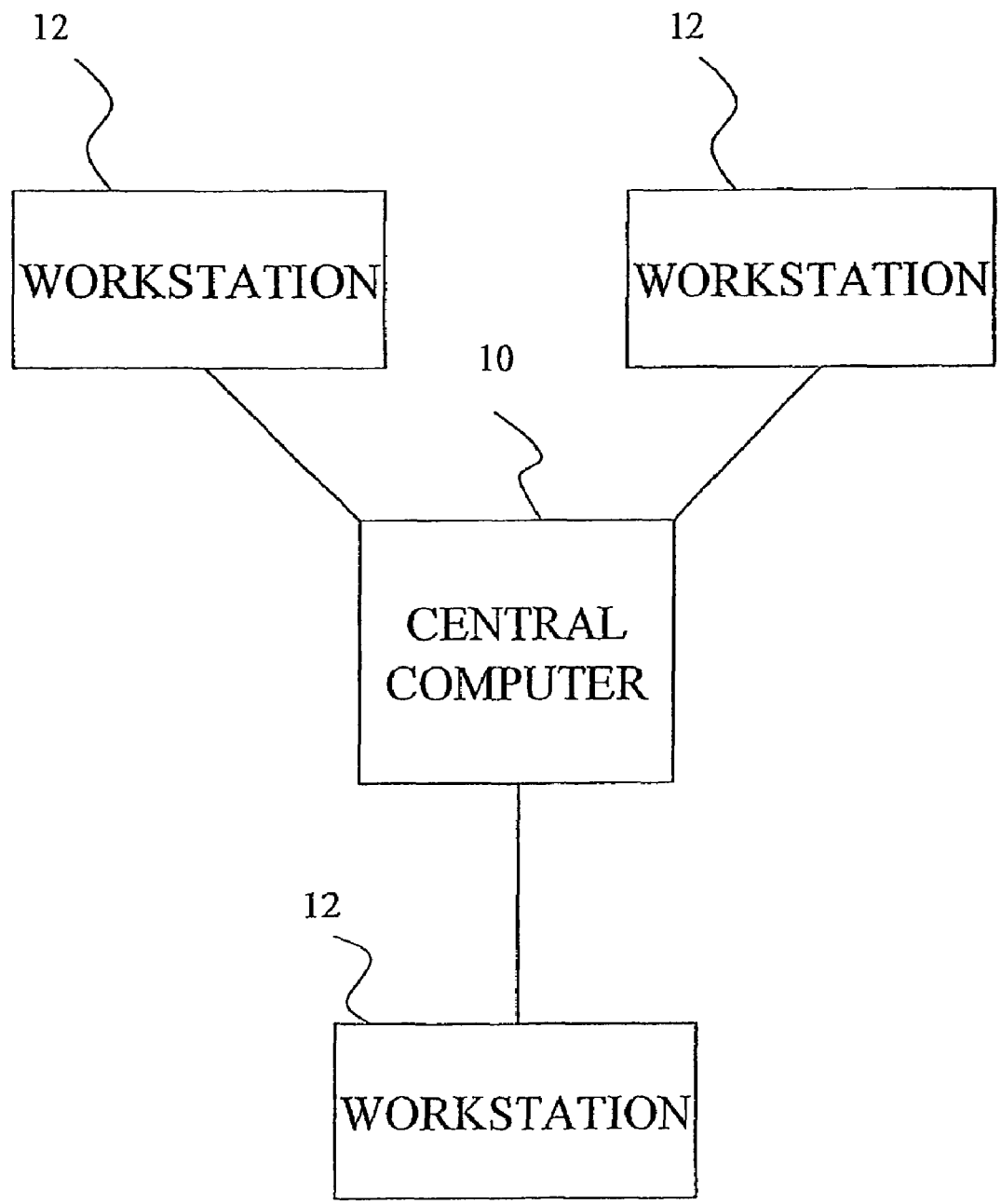
FIG. 1 is a diagrammatic overview of the system of the present invention.

Referring to FIG. 1, the present invention preferably includes a central computer 10 and a plurality of separate workstation computers 12 connected to the central computer, such as through a conventional network system, and provides an efficient method of storing information and interfacing with a user for entering, accessing and outputting information to improve documentation and workflow. In particular, the system stores medical record information such as patient information, insurance information including documentation requirements of insurance companies, timelines for calendaring events, and dictionaries of commonly or repetitively used information. The dictionaries are groups of related entries (records). They may be viewed as reference material that does not change substantially over time and which may be selected for use during entry of data or for timeline entries. The dictionaries and their use will be described further below.

The present system is also designed to provide an interface for inputting data or information previously contained on paper documents, including inputting information relating to an encounter or appointment with a patient and inputting information on business related contacts including information on patients, pharmacies, physicians, and insurance companies. The system further provides outputs which facilitate tracking of patients and their medical status, prescription writing, printing of reports, and preparation of insurance forms including electronic claim forms and HCFA-1500 forms (Health Care Finance Administration forms) used to expedite Medicare, Medicaid and private insurance benefits.

Figure 2:
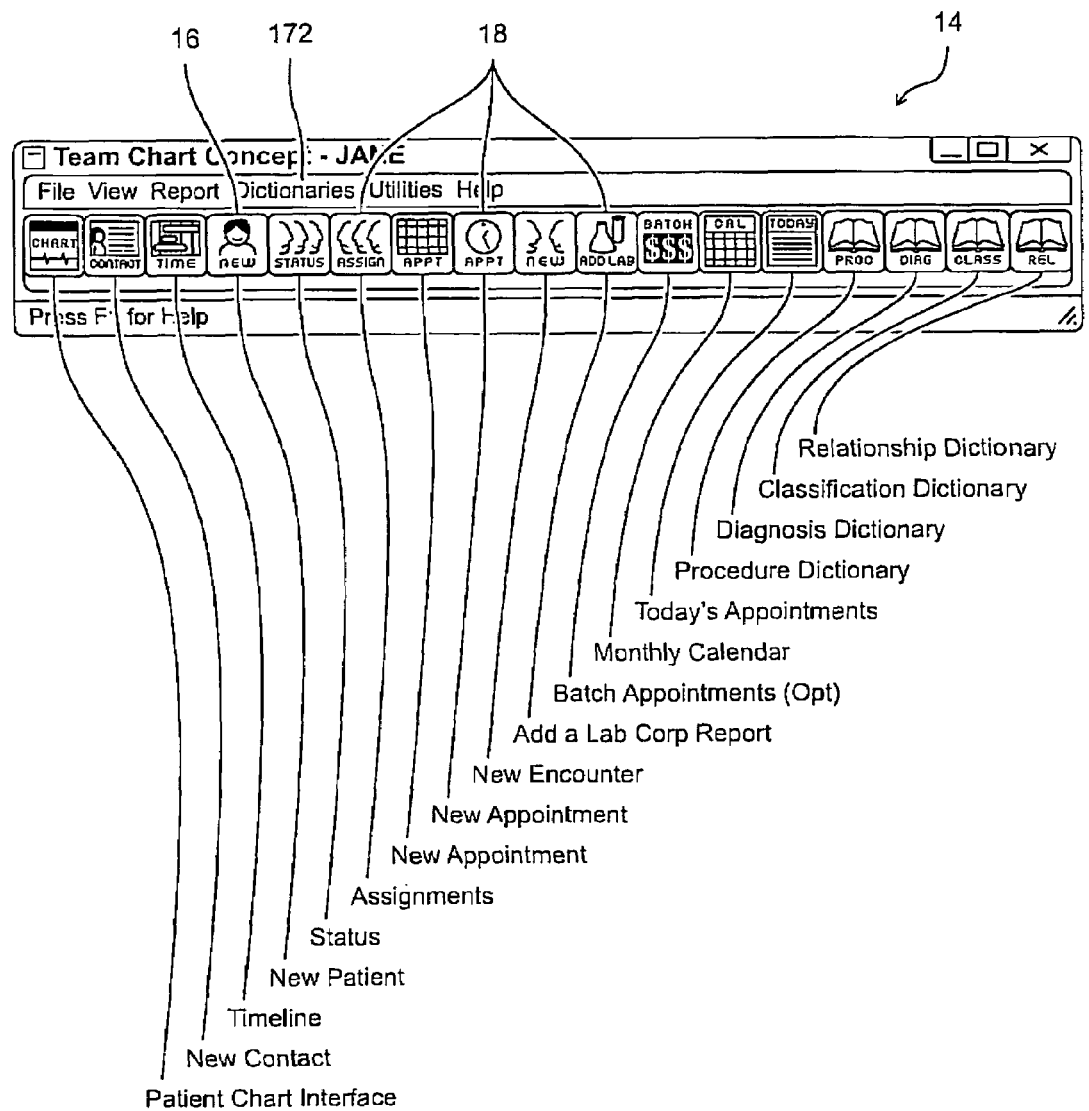
FIG. 2 illustrates a main screen for the system.

FIG. 2 illustrates a main screen 14 for the system and includes a toolbar 16 from which the most commonly used routines may be accessed. For example, buttons 18 on the tool bar 16 may be used to access appointment and calendar screens, access screens for preparing outputs such as reports, access screens for checking status of time dependent events, as well as other functions which are described below.

Figure 4:
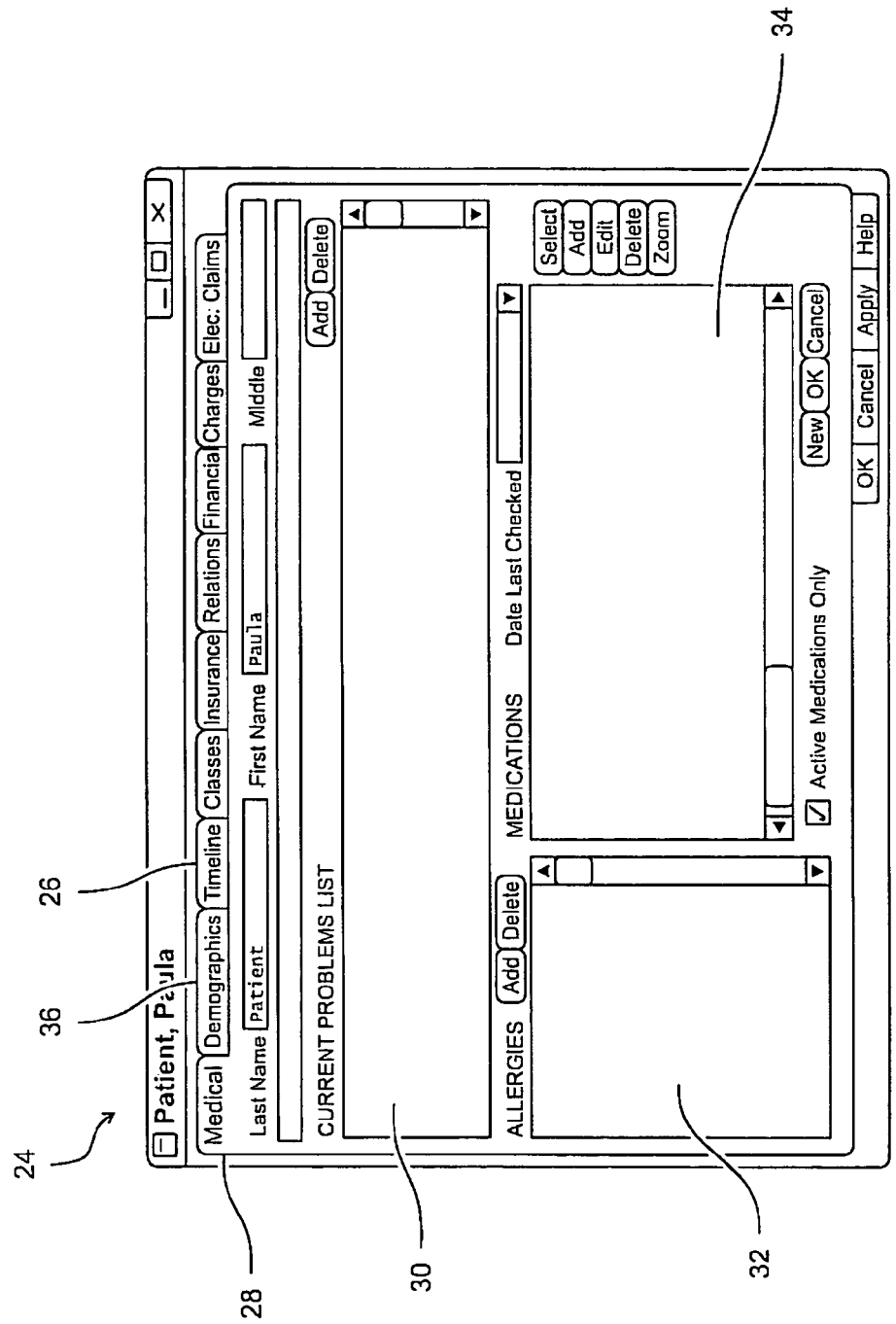
FIG. 4 illustrates a contact information dialog box for a particular patient, with a medical tab selected.
Figure 5:
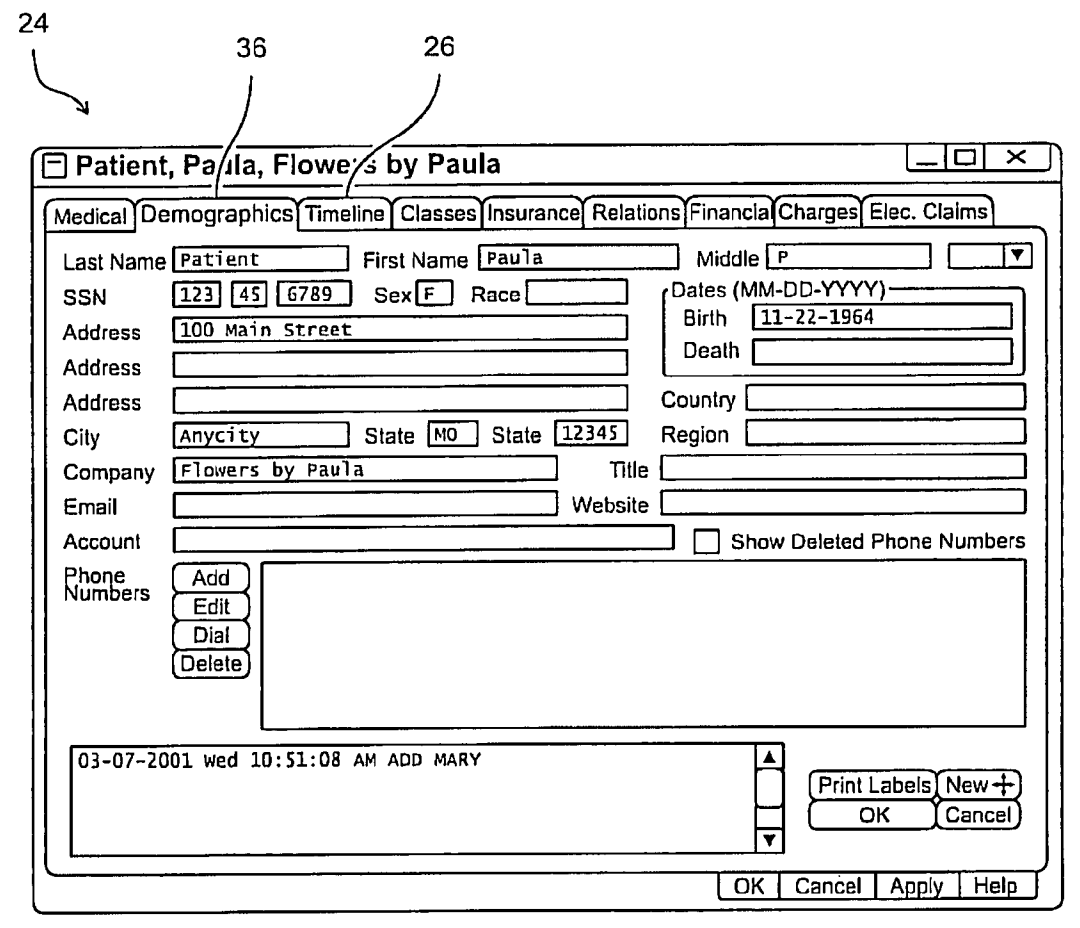

Referring to FIG. 3, an Add New Contact dialog box 20 is illustrated which may be accessed from a screen called up by the Contacts button on the toolbar 16 of the main screen 14. The Add New Contact dialog box 20 is used to input contact information, such as for a patient, pharmacy, or health care provider, and in the illustrated example shows entry of a new patient. Upon entry of information in this dialog box 20, the user presses the OK button 22, which opens a Contact Information dialog box 24 (FIG. 4). It can be seen that the Contact Information dialog box 24 includes a plurality of tabs 26 for displaying different groups of related fields for data entry. For example, in FIG. 4 the Medical tab 28 is selected for entering pertinent medical information into fields such as Current Problems 30, Allergies 32 and Medications 34. FIG. 5 shows the fields displayed upon selection of the Demographics tab 36 where pertinent contact information for the patient may be entered, such as address and phone numbers, as well as other demographic information such as birth date, social security number and employer.

Figure 6:
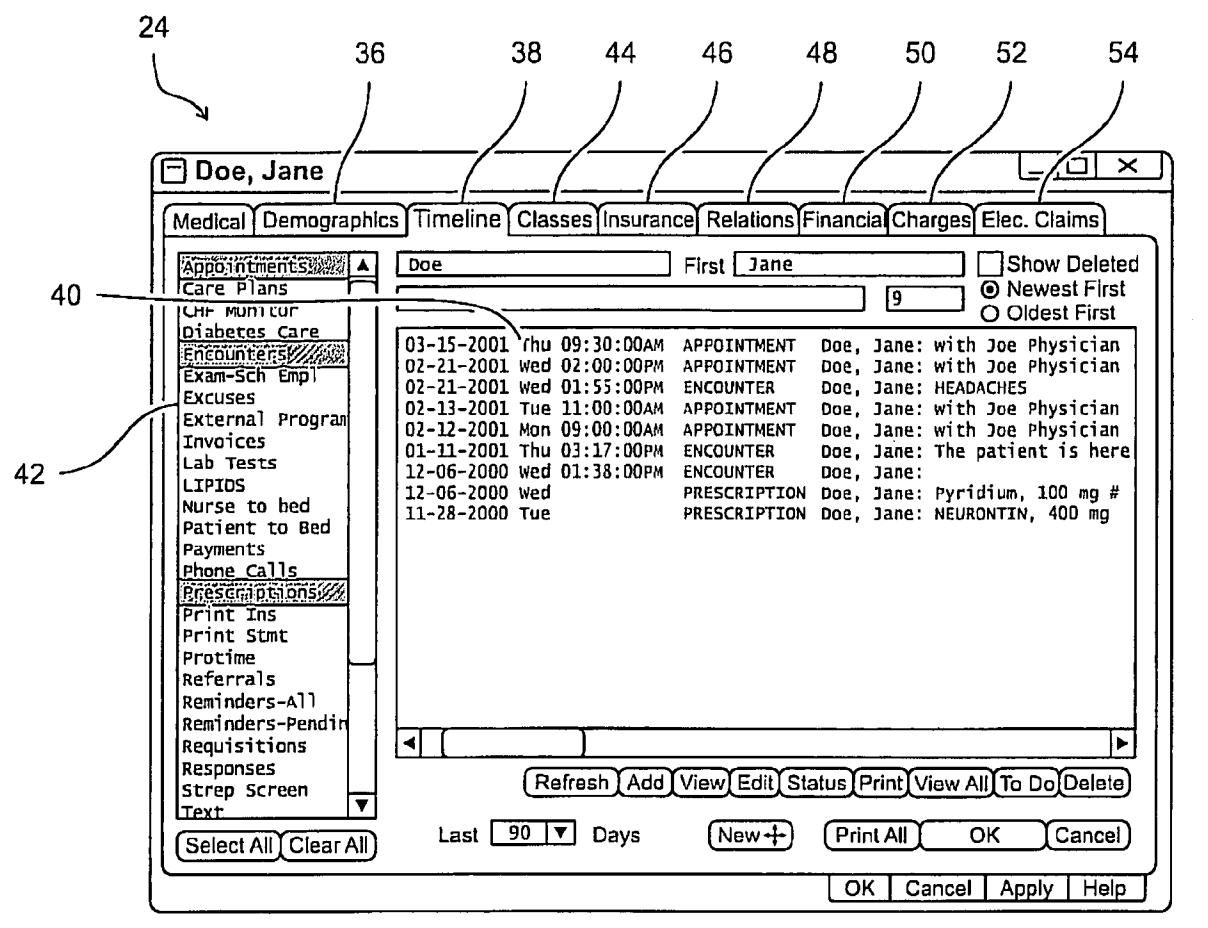

FIG. 6 shows the fields displayed upon selection of the Timeline tab 38 which includes a main list box 40 listing a chronological history of every interaction with a contact, i.e., between a patient and the medical office. The list box 42 on the left side of the Contact Information dialog box 24 contains an alphabetical list of all available timeline entry types or categories. By selecting one or more of these timeline entry types, a list of timeline entries in the main list box 40 will be displayed for the selected contact. As used herein, "timeline" refers to the collection of date/time entries stored in chronological order in the system and including appointments, encounters (as defined below), prescriptions, excuses, referrals, lab results, payments, claims made to insurance companies, patient statements, user defined timeline records, and phone calls.

Additional information entered through selection of the remaining tabs 26 on the Contact Information dialog box 24 includes: Classes tab 44—includes fields for classification and categorization of contacts, i.e., patient, physician, nurse, insurance company, employee, pharmacy, etc., and collects status information (single, married, employed, etc.) required on the HCFA-1500 form; Insurance tab 46—lists all insurance companies associated with a particular patient; Relations tab 48—documents family relationships for the contact including contact type, i.e., son, and the name of the relation; Financial tab 50—used to review financial information on the patient, such as charges, money received and balance due, and provides for printing of statements and receipts; Charges tab 52—displays charges associated with a particular patient; Elec. Claims tab 54—provides fields for entering patient defaults for use in filing electronic claims using the Electronic Media Claims National Standard Format.

The information entered in the Contact Information dialog box 24 for a patient corresponds to information typically entered in paper chart systems upon registration of a new patient. It should be understood that pertinent contact information for physicians and pharmacies, as well as other contacts such as insurance companies, may be entered from the Contact Information dialog box in a similar manner to that described for patient information.

Referring to FIG. 7, a Patient Registration dialog box 56 is further provided for entry and display of information collected on any patient in the system, and this dialog box is accessed from the toolbar 16 (New Contact button) on the main screen 14. The information in this dialog box 56 is the same as is available in various places on the Contact Information dialog box 24 (FIG. 4), and the Patient Registration dialog box 56 conveniently provides the collected patient information at one reference location. It should be noted that it is possible to enter patient registration information through either the Patient Registration dialog box 56 or the Contact Information dialog box 24.

Figure 8:
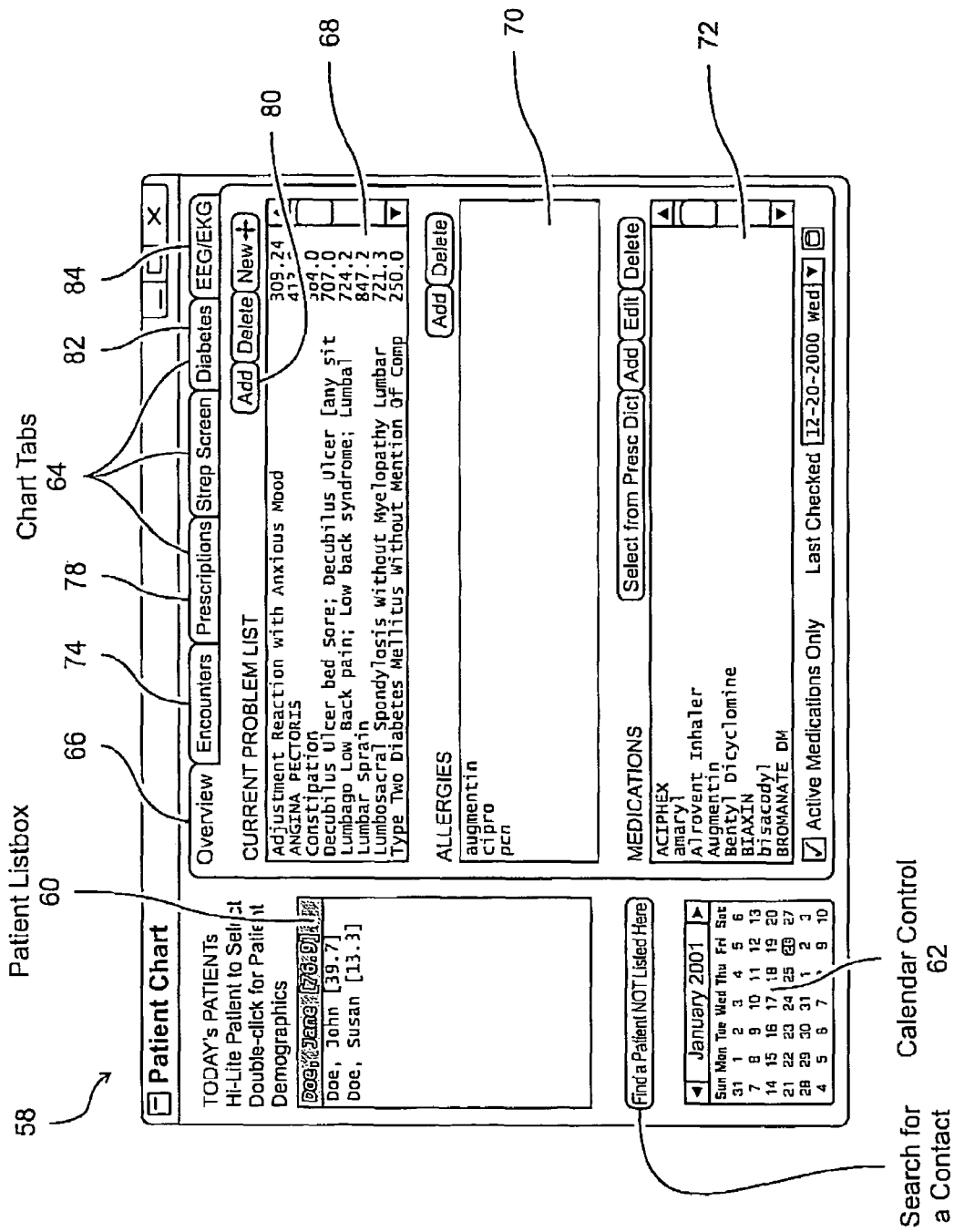
FIG. 8 illustrates a patient chart dialog box for the system, with an overview tab selected.

Referring to FIG. 8, a Patient Chart dialog box 58 is provided which is designed to generally correspond to the appearance of a paper chart, while providing enhancements available as a result of use of an electronic record system. The Patient Chart dialog box 58 generally includes a patient listbox 60, a calendar control 62, and a chart tabs area 64. The calendar control 62 specifies the date for listing patients in the patient listbox 60, and more specifically, lists patients who have an appointment or other date related activity ("timeline entry") for the selected date. The patient listbox 60 lists all patients having a timeline entry on the selected date, and a particular patient may be selected within this box to display the selected patient's chart. The chart tabs area 64 includes a plurality of tabs for displaying list boxes corresponding to different categories of medical information for the patient wherein all tabs except for the overview tab 66 are timeline-based, that is, have a date associated with the entry.

Figure 9:
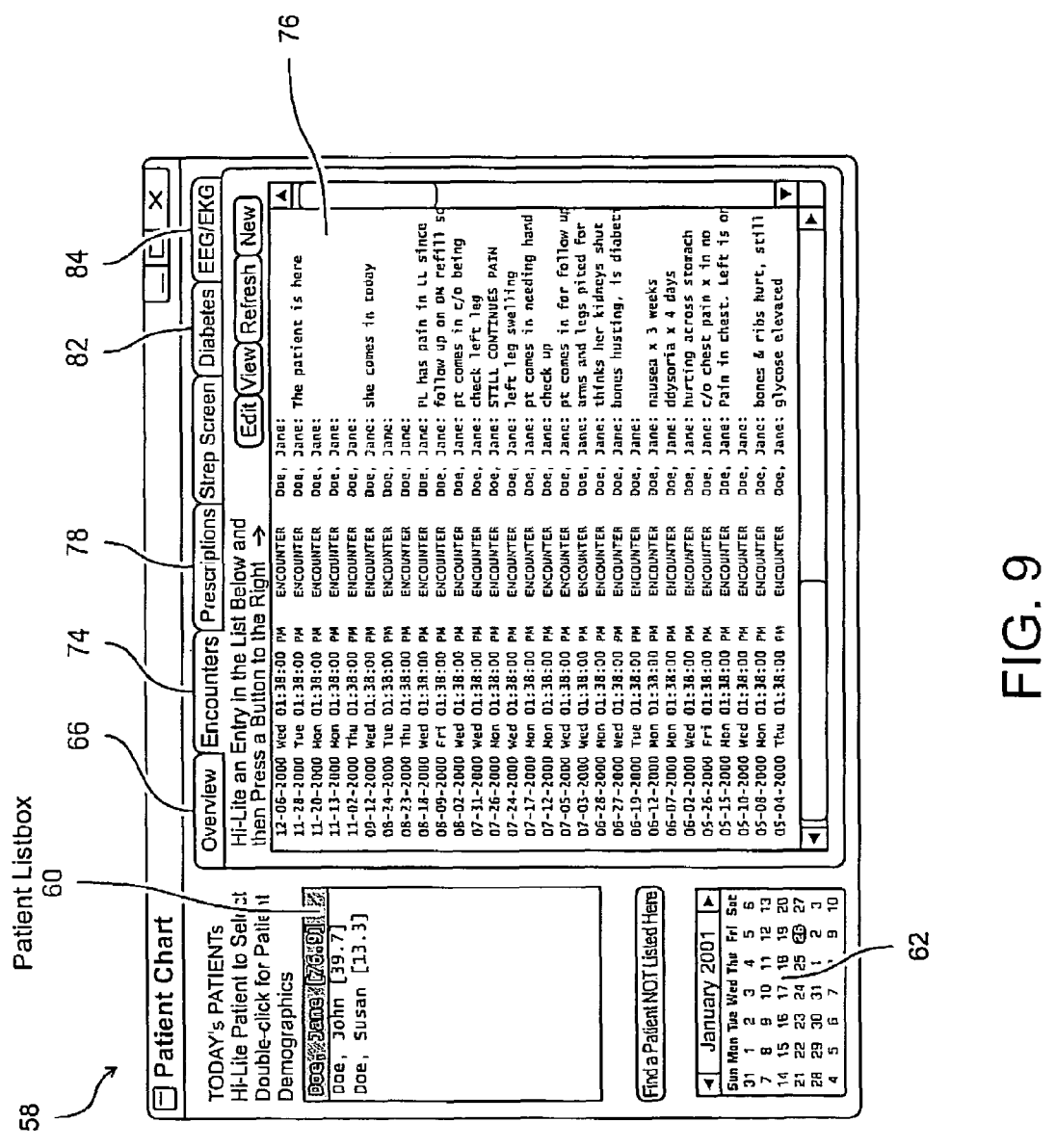

As seen in FIG. 8, the overview list box includes boxes for displaying current problems 68, allergies 70, and medications 72, which information is drawn from the patient registration information entered upon addition of the patient to the system, as well as from updates subsequently entered during patient visits ("encounters"). FIG. 9 illustrates the Patient Chart dialog box 58 with an Encounters tab 74 selected. The dialog box 76 displayed with the Encounters tab 74 provides a listing of patient encounters which are listed in chronological order, starting from the most recent encounter. As can be seen in FIGS. 8 and 9, additional tabs are included for prescriptions 78, strep screen 80, diabetes 82 and EEG/EKG 84, which are default tabs for inclusion on the Patient Chart 58.

Figure 10:
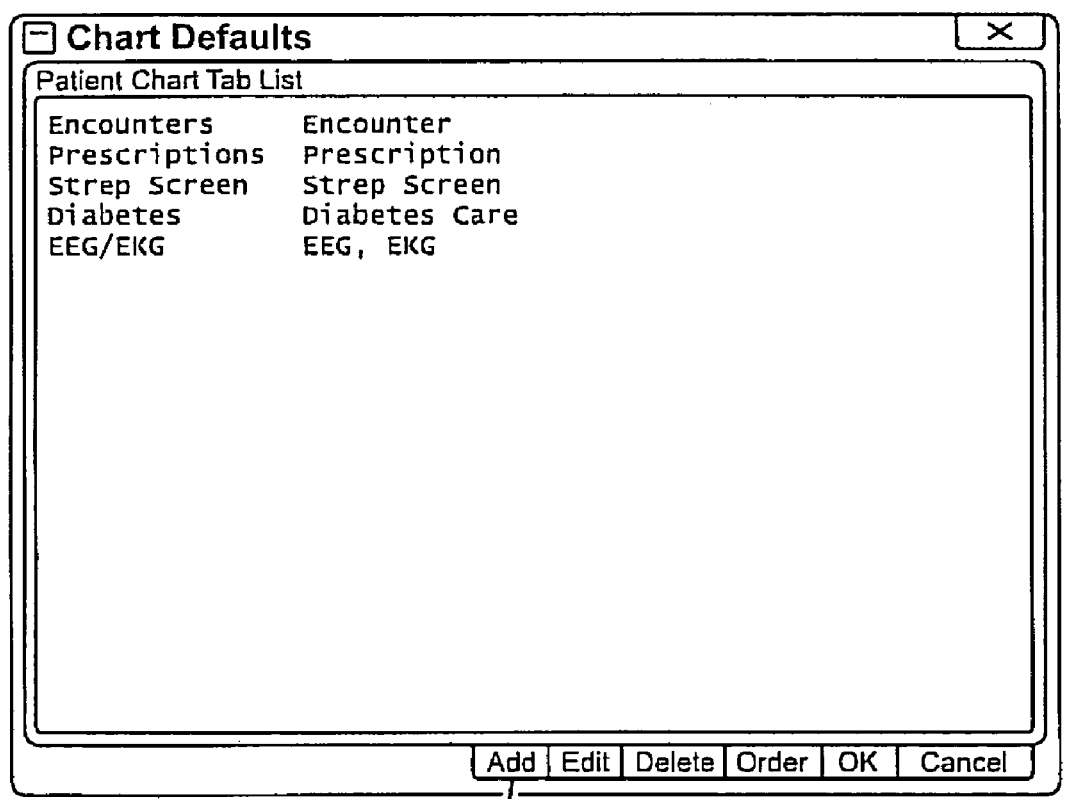
FIG. 10 illustrates a chart defaults box listing the default tabs for display on the patient chart of FIG. 8.
Figure 11:
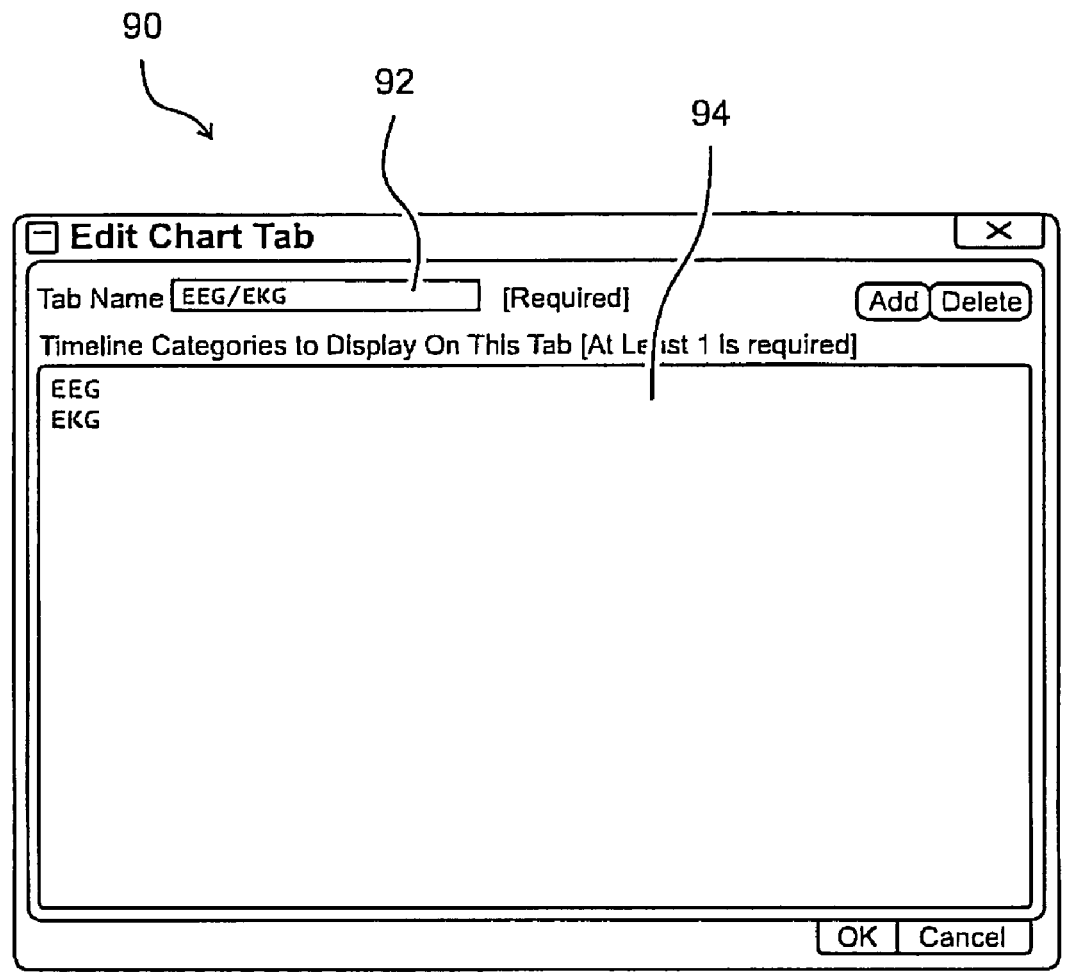
FIG. 11 illustrates a dialog box for adding a new chart tab to the patient chart of FIG. 8.
Figure 12:
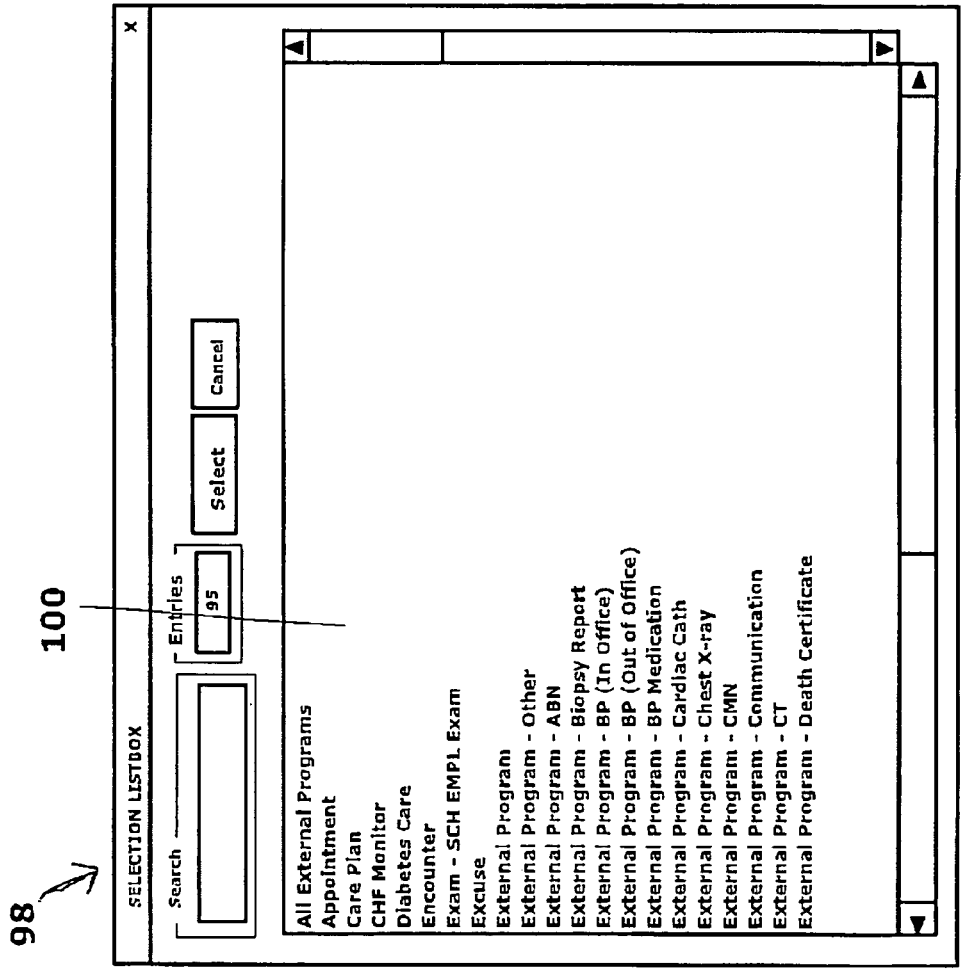
FIG. 12 illustrates a dialog box for selecting timeline categories to associate with the new tab selected through the dialog box of FIG. 11.

It should be understood that a characteristic of the present invention is provision of user capability to select tabs 64 to be displayed on the Patient Chart 58. This is accomplished by going through a series of dialog boxes illustrated in FIGS. 10-12. FIG. 10 shows a Chart Defaults box 86 which may be accessed from a utilities menu (not shown) of the system and preferably may be accessed only by the system administrator. The Chart Defaults box 86 normally includes a listing of the default tabs discussed above, and includes an Add button 88 for accessing the Edit 1 Chart Tab dialog box 90 illustrated in FIG. 11. In this dialog box 90, an edit field 92 is provided where a name for the new tab to be added is defined by the user, and the list box 94 for this dialog box 90 lists the timeline categories to be associated with the new tab. Selecting the Add button 96 from the Edit 1 Chart Tab dialog box 90 accesses a Selection dialog box 98, as shown in FIG. 12, which includes a list box 100 listing all possible timeline categories for the system, and any of the timeline categories may be selected for association with the new tab. It should also be noted that additional, user defined timeline categories may also be included in the Selection dialog box 98. Further, multiple tabs may be added to the Patient Chart 58 through the above-noted steps to provide ready access to the desired timeline categories or groups of categories. Accordingly, it should be apparent that the Patient Chart 58 for the system may be conveniently designed by the user to include selected timeline categories, and thereby accommodate the particular needs of the user.

Figure 13:
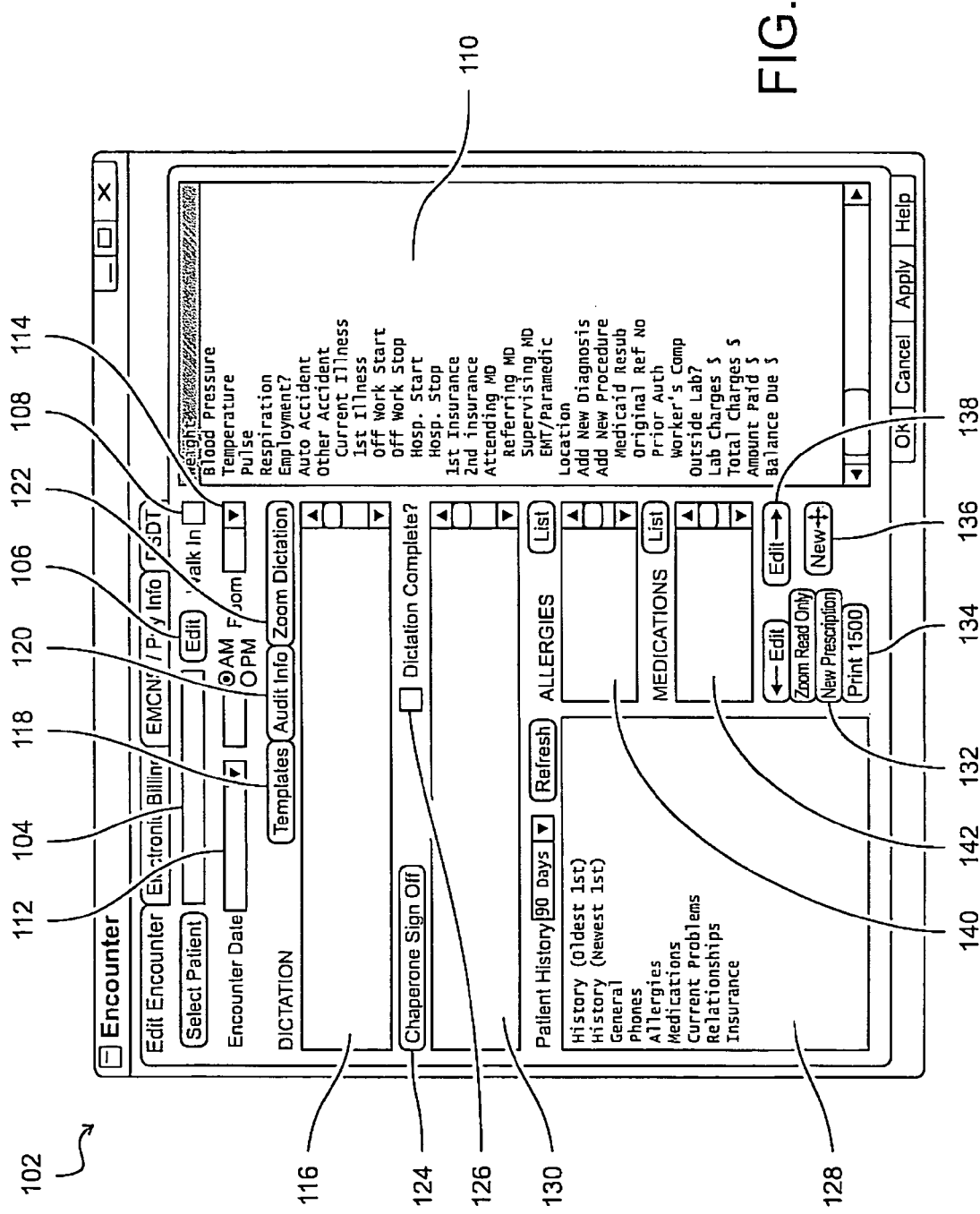
FIG. 13 illustrates an encounter dialog box used to define a patient encounter.

Referring to FIG. 13, an Encounter dialog box 102 is illustrated which is used to define a patient encounter. An encounter is a visit which is typically an examination of a patient by a physician, and encounters are billable events wherein electronic claims and HCFA-1500 forms are tied back to a specific encounter. The Encounter dialog box 102 provides a tool for gathering and accessing multiple categories of information about the patient. In particular, the encounter may include information on vital signs, physician dictation, insurance company information, charges, procedures, diagnoses, and HCFA-1500 form fields such as accident, worker's compensation, etc. The controls on the Encounter dialog box are defined as follows:

(a) Select Patient 104—For selecting a patient from the list of contacts in the system;

(b) Edit 106—If a Patient has been selected, pressing this button invokes the Contact Information dialog box 24 for the given patient;

(c) Walk-In 108—This box is checked if the Patient did not have an appointment;

(d) List 110—The list box on the right one-third of this dialog box contains a list of all Fields associated with the current encounter. Any field in this list box may be selected in order to change its contents. For example, selecting 'Add New Diagnosis' enables the user to add a new diagnosis to this encounter, selecting 'Add New Procedure' enables a user to add a new procedure to this encounter;

(e) Encounter Date (and time) 112—This box specifies the starting date and time of the encounter;

(f) Room 114—This box specifies the examination room number that this encounter will take place in. This is an optional field that may be used to help control patient flow through a medical facility;

(g) Dictation 116—This box is for entry of the physician's dictation and the dictation may be directly typed into this field. There are three buttons that aid in entering dictation:

(i) Templates 118—Selecting this button enables the user to access a Template dialog box (not shown). Templates are pre-written phrases organized in such a way to let the physician quickly enter dictation;

(ii) Audit Info 120—Selecting this button enables the user to access the system auditor which will examine the dictation for Medicare compliance. The physician can quickly see if his or her dictation supports the office/hospital visit procedure code selected for the current encounter;

(iii) Zoom Dictation 122—Selecting this button enables the user to display the dictation in a large dialog box for easy viewing;

(h) Chaperone Sign Off 124—This is an optional field whereby a chaperone who has accompanied the physician during the encounter can enter a password to sign off that the physician was never alone with the patient;

(i) Dictation Complete 126—This box is box is checked once the dictation is complete and ties back to the Timeline dialog box, so that a physician can quickly see which encounters still require dictation;

(j) Patient History 128—This list box contains patient demographics, insurance, phone numbers, allergies, medications, current problems, family members, and all timeline entries for the selected patient. Any entry in this list may be selected in order to be displayed in a read-only field 130 immediately above the words 'Patient History'.

(k) New Prescription 132—This button is selected to make a new prescription for the selected patient;

(l) Print 1500 134—This button is selected to print an HCFA-1500 Form Insurance Claim for this encounter;

(m) New 136—This button is selected to create a new Timeline entry for the selected patient;

(n) Edit 138—After selecting an entry in the list box on the right one-third of this dialog box, this button may be selected to edit that entry;

(o) Allergies 140—All of the selected patient's known allergies are listed here. Selecting the 'List' button enables the user to update and/or view the allergies;

(p) Medications 142—All of the Patient's known medications are listed here. Selecting the 'List' button enables the user to update and/or view the medications.

As noted above, diagnoses and procedures may be added to the encounter by selecting these fields in the list box 110. FIG. 14 illustrates a dialog box 144 listing commonly used diagnosis codes and from which diagnosis codes appropriate for the current encounter may be selected. FIG. 15 illustrates a dialog box 146 listing commonly used procedures and from which procedures appropriate for the current encounter may be selected. The selected diagnoses and procedures will then be displayed in the list box 110 of the Encounter dialog box 102.

Figure 16:
FIG. 16 illustrates a dialog box for providing a user with procedure code audit information.

If an 'office visit' or 'hospital visit' is selected for the procedure, and the code associated with the visit corresponds to one of a preselected group of procedure codes the system will display a further dialog box 148, such as is illustrated in FIG. 16, which box will automatically notify the user as to which office or hospital visits include enough documentation to support the selected procedures. This feature provides an automatic Medicare audit check in which 'Yes' label is associated with those procedures for which the entered documentation will likely pass the requirements of Medicare, and a 'No' label is applied to those that likely would not pass. This feature is useful to facilitate submitting claims for the highest available reimbursement level as well as to notify the user of possible need to include further documentation to support a higher level procedure.

Figure 17:
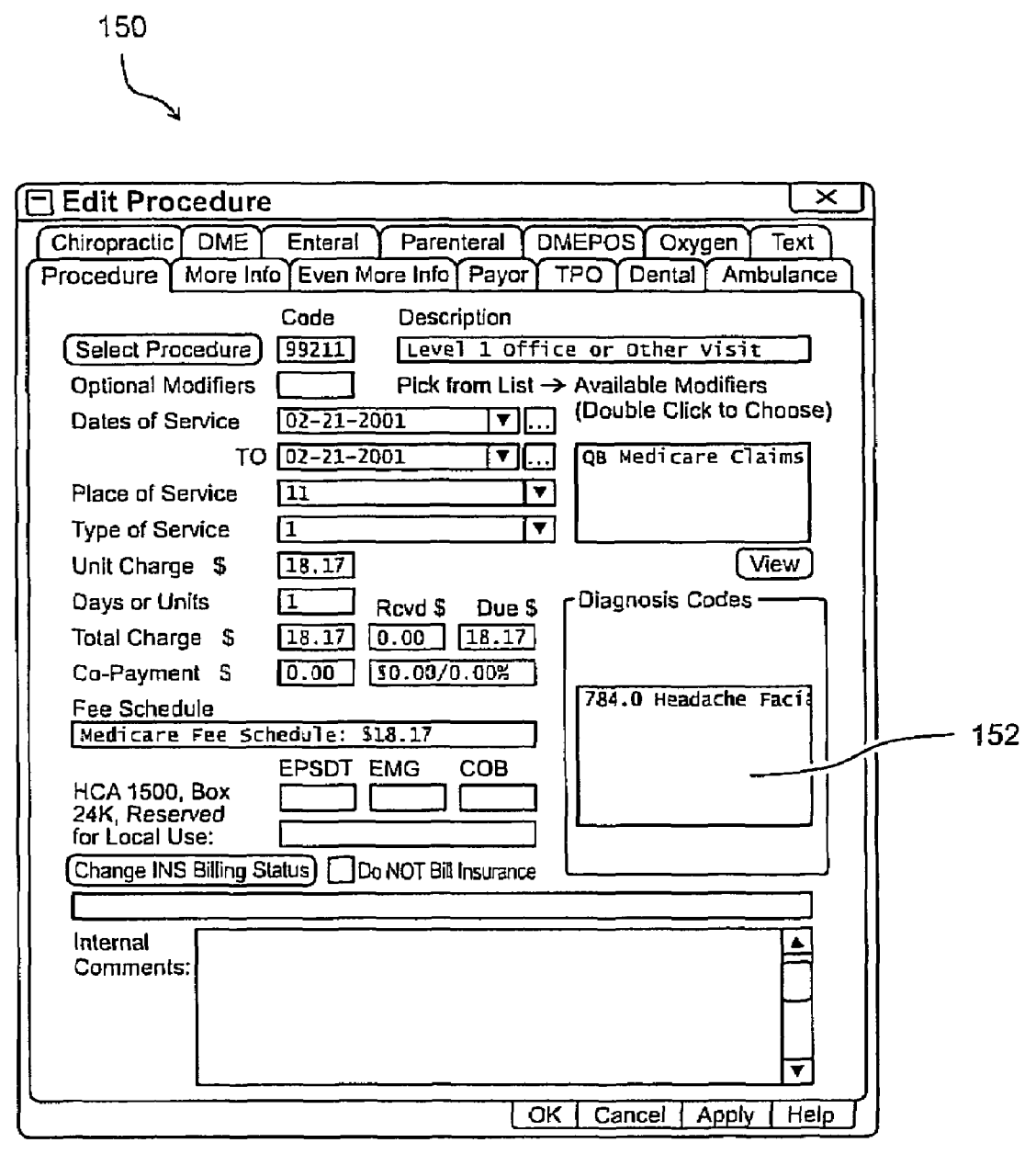

Subsequently, after the procedure is selected, based on an audit, control passes to an Edit Procedure dialog box 150, as illustrated in FIG. 17. At this dialog box 150 defaults are filled in for the most commonly used fields, and the user is required to indicate supporting diagnoses for the selected procedure. In addition, the diagnosis codes 152 are identified and ordered by the user in the order of most important to least important such that the most important diagnoses will appear at the top of the list. Upon completion of this dialog box, the user is returned to the Encounter dialog box 102.

As noted above, the dictation entered by the physician may be input to the Encounter dialog box 102 through use of templates provided in a Template dialog box. The Template dialog box essentially provides pre-written phrases which may be selected as text for the physician to enter as dictation. The audit function of the system is designed to operate in conjunction with the pre-written phrases to enable the audit function to recognize the documentation entered through dictation and determine whether it meets Medicare requirements for the current procedure code selected for the encounter. Further, the physician may use the Audit Info button 120 to inquire whether the entered dictation is sufficient to support the selected procedure code. In this respect it should be noted that the Encounter dialog box 102 is preferably accessible by the physician concurrently with the patient encounter, whereby the patient is present in the event the physician finds that additional documentation relating to an examination or other information from the patient is required for support of the selected procedure code.

Figure 18:
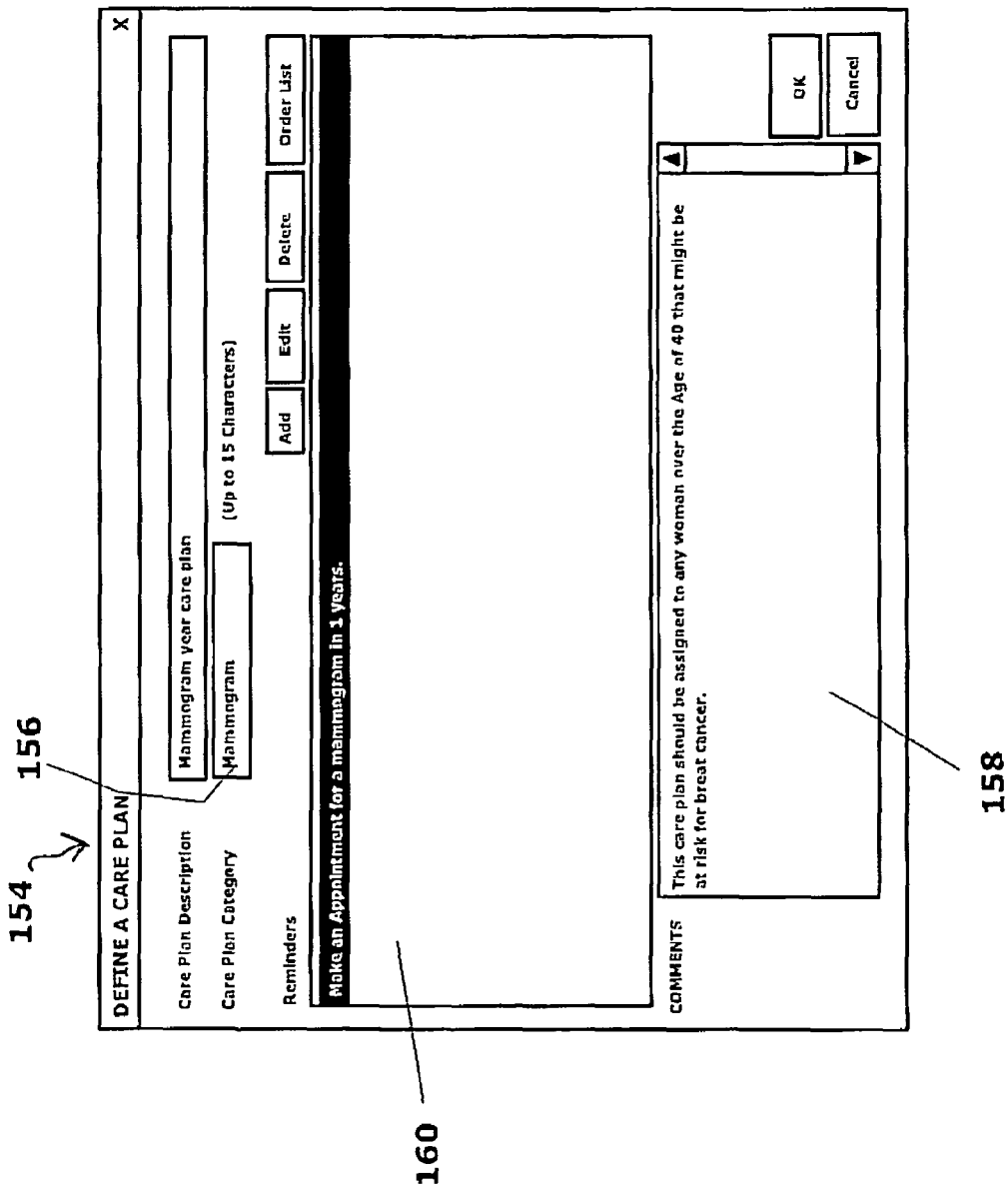
FIG. 18 illustrates a dialog box for enabling a user to define a care plan.
Figure 19:
FIG. 19 illustrates a dialog box for entering details of a reminder for inclusion in the care plan of the dialog box illustrated in FIG. 18.

In another aspect of the present system, a care plan may be prepared for a patient, or assigned to a patient from a list of saved care plans. A care plan is a future plan of action on behalf of a specific patient and is formed by a group of reminders wherein a reminder is created to remind the user of a timeline event which will occur at a particular date and time in the future. More specifically, a care plan provides the user, such as a physician, with a proactive tool for tracking a patient's condition over time and provides call-ups or reminders at time intervals and frequencies predetermined by the user. For example, referring to FIG. 18, an initial Care Plan dialog box 154 is shown which enables the user to define a care plan, such as a five year care plan for women who need to have a mammogram on a yearly basis, and includes an edit field 156 for defining a care plan category, entering a care plan description (comments 158) and entering reminder events 160. FIG. 19 illustrates a dialog box 162 for entering details of the reminder such as length of time to the initial reminder (1 year), number of times the reminder should be repeated (4 additional reminders), and time interval between reminders (1 year). FIG. 20 illustrates the dialog box 162 with a further reminder which would be included in the current example and reminds the user that the care plan is expiring after five years, and consider implementing an appropriate further care plan. It should be understood that a variety of care plans may be created to cover different conditions, such as obesity, high cholesterol, hypertension, etc.

Care plans are incorporated into a particular patient's timeline by referencing the list of saved care plans, in particular referencing a care plan dictionary, and selecting appropriate care plans for the particular patient. The care plan time entries will then appear when the Timeline tab 38 is selected in the Contact Information dialog box 24 (FIG. 6).

As noted previously dictionaries include information which does not change substantially over time, and typically includes information which may be referenced for entry a plurality of times during use of the system. In the case of care plans, different patients having similar conditions are often placed on similar schedules for treatment and follow-up, and the provision of a care plan dictionary reduces time required for data entry and facilitates scheduling of future encounters related to the condition. Other dictionaries included with the system and their descriptions comprise the following:

Procedure Codes Dictionary—stores all procedure codes, descriptions, and pricing information. Procedures are assigned to encounters to document a billable service performed by a medical office on behalf of a patient.

Diagnosis Codes Dictionary—stores all diagnosis codes, and descriptions. Diagnoses are assigned to encounters to document a medical diagnosis of a patient's current health.

Classification Dictionary—stores classifications that may be assigned to a contact in order to provide a description of the type of contact. Examples of classifications include patient, physician, nurse, insurance company, cardiology MD, health care provider, lab, etc.

Prescription Dictionary—stores a collection of standard prescriptions that the user can quickly copy from. Use of the prescription dictionary enables the user to only have to type in the medication, dosage, and directions for a prescription one time.

Requisition Dictionary—stores a list of all of the commonly used requisition types in your office, where a requisition is an in-house request to perform some type of service on behalf of a patient and comprises an entry in a patient's timeline.

Billing Codes Dictionaries—stores billing code information and is broken down into five different billing codes dictionaries:
 1. Insurance Class Dictionary.
 2. Payment Codes Dictionary.
 3. Medicare Claim Adjustment Codes.
 4. Medicare Reference Codes.
 5. Medicare Inpatient/Outpatient Codes.

Status Dictionaries—used to maintain the past and current statuses of three different classes of events. There are three different status dictionaries:
 1. Appointment Status—used to maintain the current and past statuses of appointments (e.g. scheduled, late, canceled).
 2. Encounter Status—used to maintain the current and past statuses of encounters (e.g. scheduled, nurse, doctor, check-out). Useful for tracking patients after entry to a medical facility wherein each patient encounter in the facility would be assigned one of the following statuses: Scheduled, Exam Room, Doctor, Check Out, and Discharged.
 3. User Defined Status—used to maintain the current and past statuses of user defined timeline records, such as lab tests (e.g. scheduled, in-process, complete).

HCFA-1500 Codes Dictionaries—stores code information for inclusion in the HCFA-1500 form including: 1) Place Of Service Codes, and 2) Type Of Service Codes.

Referral Dictionary—stores instructions used when referring a patient to another office or physician. Such instructions may need to include steps for a patient to follow in preparation for procedure, such as a gall bladder ultrasound, or upper GI, and these instructions are included in the referral dictionary.

Relationship Dictionary—stores a defined relationship or association between two contact, and typically stores family ties, such as parent, brother, aunt, etc.

Exam Room Numbers Dictionary—stores a list of exam room numbers or identifiers for exam rooms in a medical facility, and in particular in a smaller practice.

Phone Descriptions Dictionary—stores the different types of phone descriptions that may need to be documented for a contact. Phone descriptions include home, office, fax, cell, emergency, etc.

Appointment Reasons Dictionary—stores a list of the most common reasons patients make an appointment with a medical facility.

Physicians Dictionary—stores information on physicians or other health care providers that may be assigned identification numbers by insurance companies and/or governing medical boards. The physicians dictionary is used to keep track of insurance identification numbers (e.g. PIN, GRP), assignment status, and similar information.

Equipment Dictionary—stores information for tracking equipment and machinery in a medical facility. Enables assignment and tracking of equipment to patients, physicians, nurses, rooms, departments, floors, etc.

Location Dictionary—stores a list of locations in a facility and including information such as status of use. This dictionary and is particularly intended for use in tracking rooms or locations in larger facilities such as hospitals which may have several buildings, wings and floors.

Assignment Dictionary—stores information relating to a temporary association between two entities and this dictionary is typically used in a hospital setting. Examples of assignments include assignment of a patient to a bed, assignment of a nurse to a patient, assignment of a nurse to a floor/wing/unit/department, and assignment of equipment to a room.

Fee Schedules Dictionary—stores fee schedule for use in setting different prices for the same procedure or miscellaneous charge. For example, the user may choose to charge Medicaid patients one price for an office visit, commercially insured patients another price, and private-pay patients yet a third price.

Miscellaneous Charges Dictionary—stores a list of items that should be charged directly to a contact, and such as items which are not necessarily medically related, i.e., a bill for making several copies of a patient's medical records.

Accordingly, it can be seen that the dictionaries for the present system enable the user to configure the system to the user's particular needs, such as by including certain desired items through edits to the dictionaries, or by selecting certain items from the dictionary to be implemented, such as in a patient timeline. Further, additional dictionaries may be created by the user to meet the user's particular needs, and the present system is particularly conducive to development of the dictionaries as the system is used, such as through the development of care plans administered to the patients of the user.

In a further aspect of the invention, a user may set up user defined timeline records which include computed fields. The computed records incorporate raw patient data collected and stored in the system and correlate the patient data to potential risk for particular illnesses or health problems. A potential risk is determined from a medical algorithm which is typically defined by either an equation or a series of equations conditionally related to each other, where the equations generally operate on numeric risk factor values associated with the particular illness or health problem. For example, a user may use the present system to provide a computed user defined record for assessing patient risk for such illnesses as coronary artery disease, stroke, diabetes, lung disease, kidney disease and cancer, among others.

The information stored in the computed records comprises computed fields containing values obtained from processing entered information. Further, the calculations for obtaining the values of the calculated fields will typically be performed based both on information entered at the time of each patient encounter and on demographic information (i.e., information entered into the system when the patient record is initially set up). For example, a patient's risk for cardiovascular disease may be calculated based on an established clinical calculation, such as based on the Framingham 10-year risk calculator developed by the National Cholesterol Education Program, where the risk factors included in the Framingham calculation comprise age, sex, cholesterol levels, blood pressure and smoking habits.

Similarly, a formula may used by the present system to monitor kidney function. For example, the National Kidney Foundation has developed a formula for an approximation of glomerular filtration rate requiring inputs of patient gender, age, blood urea nitrogen, serum creatinine, and serum albumin levels. The input information is readily available from a blood test and patient demographic information; however, the formula is relatively complicated and not easily integrated into a paper management system. Accordingly, calculations useful for identifying onset of illnesses are often not integrated into a medical practice due to the complexity and time involved. The present system provides a mechanism for processing information normally gathered for a patient encounter and making calculated health measurements readily available.

Figure 21:
FIG. 21 illustrates a dialog box for defining a calculated user defined record.

FIGS. 21-27 illustrate an implementation of the computed user defined records for the present invention. Referring initially to FIG. 21, a Define User Defined Timeline Record dialog box 170 is illustrated for defining a computed user defined record, and is accessed via the Dictionary button 172 on the main screen 14 (FIG. 2). The dialog box 170 includes a record description field 174, which in the present example is "Lipid Monitoring" to identify a record for calculating the relative risk of cardiovascular disease using the above-noted Framingham 10-year risk calculator. The Define User Defined Timeline Record dialog box 170 further includes a listing 176 of fields defined for use in performing calculations and for providing calculation results. In the example, the fields 178 for the user defined record are numeric input fields, such as may be entered from blood test results providing cholesterol measurements, and the fields 180 are each computed output fields.

Referring to FIG. 22, a Define A Computed User Defined Field dialog box 182 is illustrated corresponding to the "FRS % 10 yr risk" computed field 184 in FIG. 21. This dialog box 182 illustrates a portion of the condition statements 186 required to determine a final risk factor number. It can be seen that the computation includes demographic information (i.e., "sex") as well as input from other computed fields (i.e., "TOT frf"). Also, it should be understood that values from other computed fields 180 are each defined separately through the Define A Computed User Defined Field dialog box 182.

Figure 23:
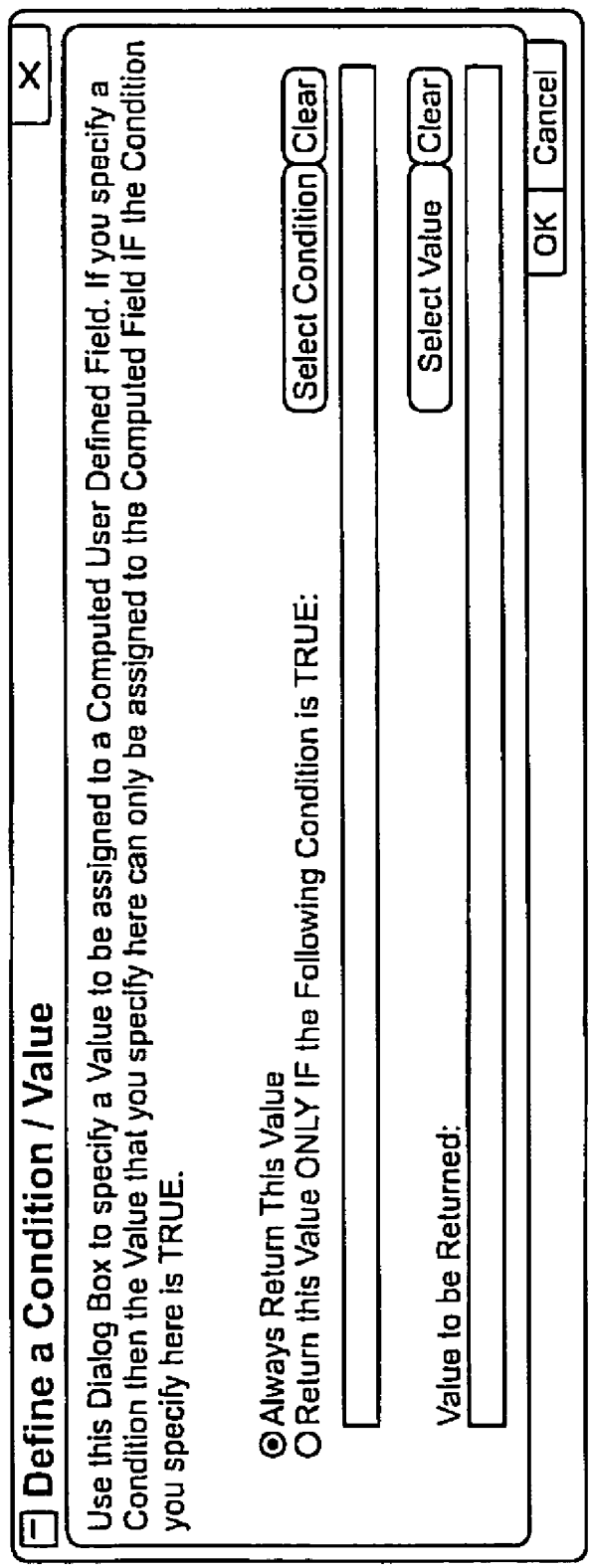
FIG. 23 illustrates a dialog box for forming condition/value statements for the user defined field.
Figure 24:
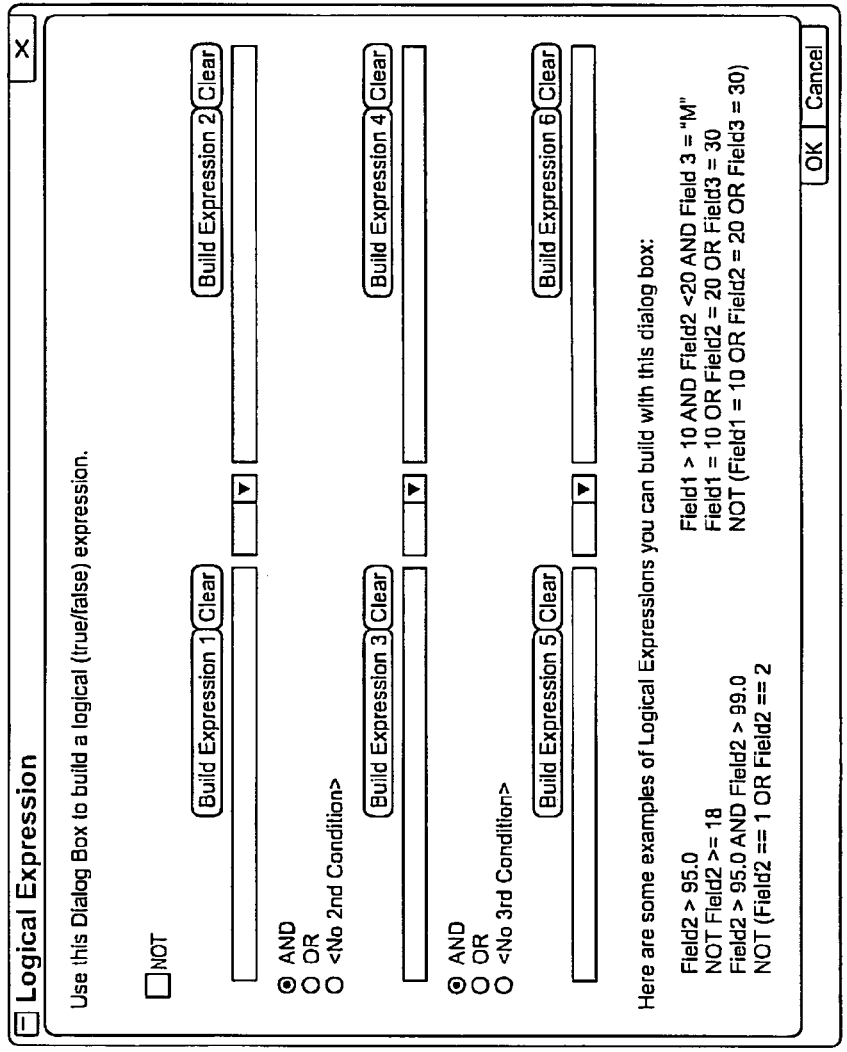
FIG. 24 illustrates a dialog box for forming logical expressions for the user defined field.
Figure 25:
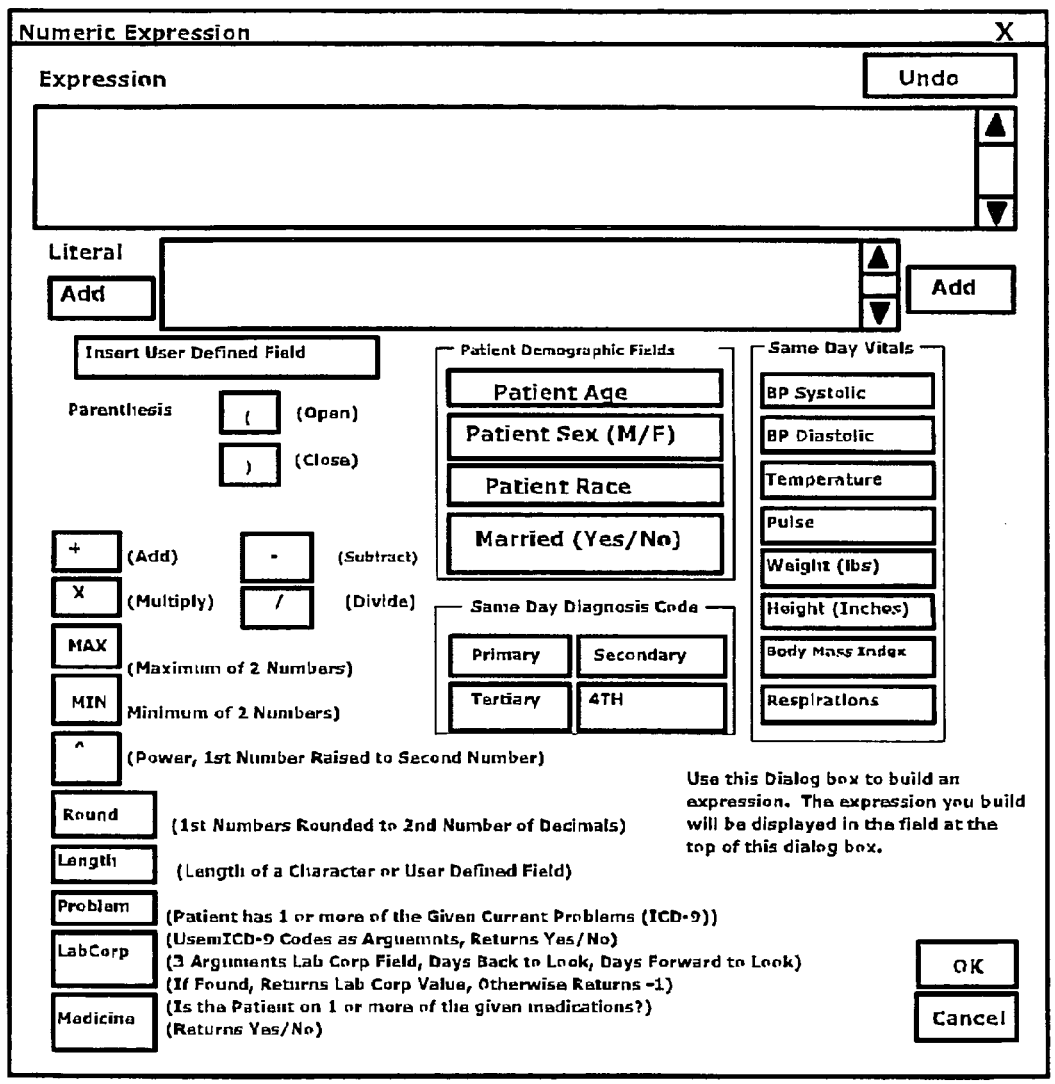
FIG. 25 illustrates a dialog box for forming numerical expressions for the user defined field.

In order to facilitate the step of preparing formulae for the dialog box 182, additional dialog boxes are preferably provided. For example, FIG. 23 illustrates a dialog box 188 for facilitating formation of condition/value statements, FIG. 24 illustrates a dialog box 190 for facilitating formation of logical expressions, and FIG. 25 illustrates a dialog box 192 for facilitating formation of numerical expressions.

It should be understood that no one particular equation is required for implementing the present invention. Further, it is contemplated that the equations for the computed user defined fields 180 may be changed or updated as additional developments are available for calculating heath risks or for providing other indicators of health.

FIG. 26 illustrates a Report Output dialog box 194 provided by the present system, in which the example illustrates a report for an individual patient, listing 10 records for a specified time range. The illustrated output provides a listing of results for monitoring FRS % 10-yr risk wherein the output can be used to monitor the progress of the patient at controlling cardiovascular risk. The output report could alternatively be generated to report on all patients in a clinic, for example, where the output report can be used to monitor the overall success of the clinic at reducing health risks. It should be noted that the output may be configured to show the particular information of interest. For example, the illustrated output shows FRS % 10-yr risk values in combination with associated cholesterol levels. An alternative report format may include display of other risk factors affecting the final output risk value instead of, or in addition to, the cholesterol levels. In addition, the output of the report can be sorted based on particular selection criteria, such as personal patient demographics or financial demographics of the patients, for example based on differences in the insurance coverage of the patients.

It should be noted that the information in the report output dialog box 194 is automatically updated as the input data is changed such that a current report may be viewed during a patient encounter. Accordingly, the physician, as well as the patient, may be provided with immediate feedback on any corrective measures taken to improve the health risk of the patient, such as a change in diet implemented at an earlier encounter. The provision of an immediate measure of a patient's health risk, provided at the time of an encounter, such as a visit to a clinic, is valuable in providing an immediate motivation for the patient to make changes for reducing the risk level, i.e., stopping smoking and losing weight. Further, the system enables the treating physician to enter a change, while in the patient's presence, such as change from smoking to non-smoking, to show the patient the projected risk reduction from implementing the change. Also, the report is capable of providing an output for showing the physician and patient the risk factors from multiple encounters, thereby providing for tracking of changes in patient health over time. Since patient dependent changes to risk factors largely rely on the motivation of the patient to put the change into practice, the present system provides a significant tool for encouraging a patient to implement a change for reducing the onset of a preventable disease.

Figure 27:
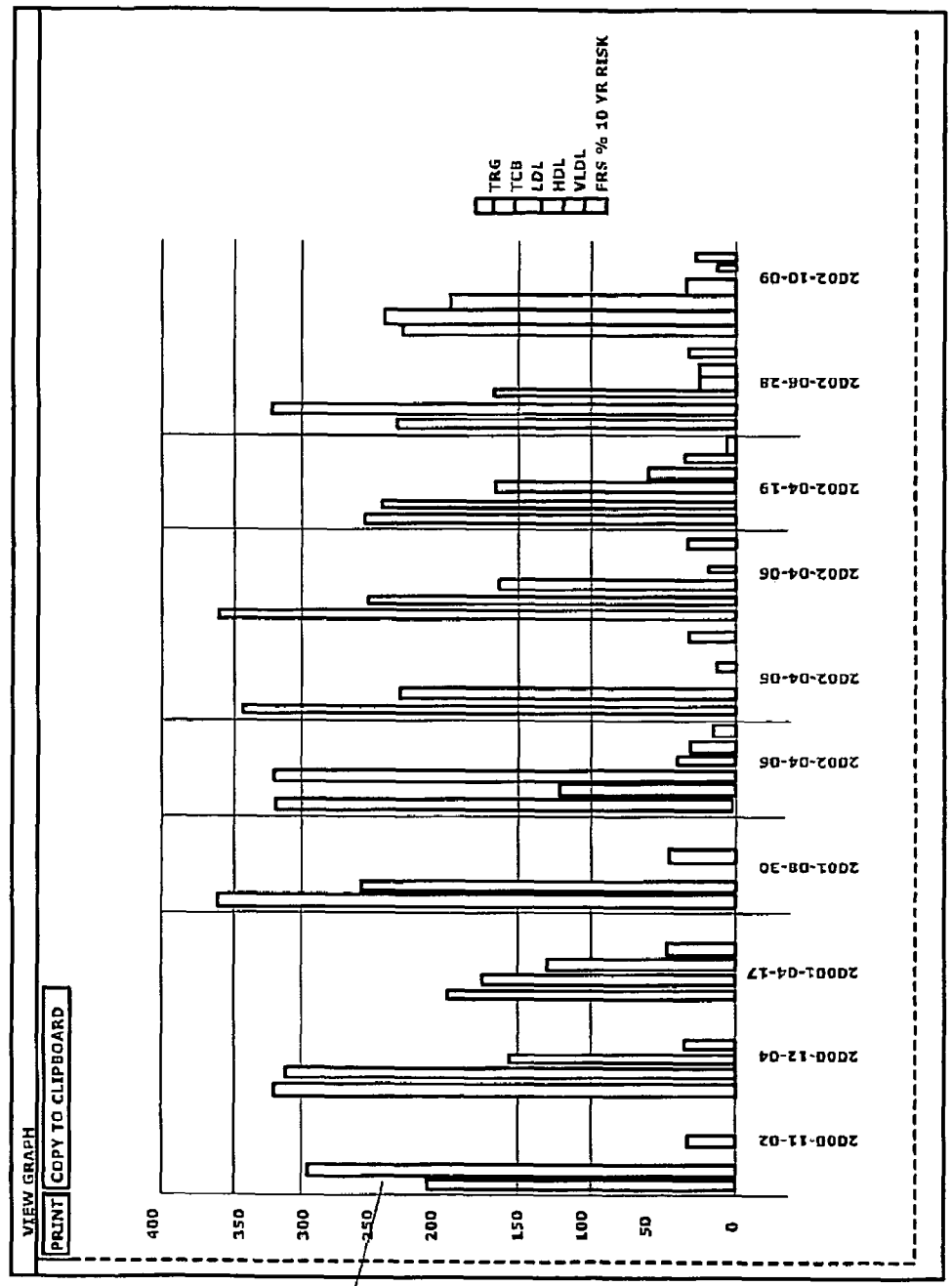
FIG. 27 illustrates a graphical output of the report output shown in FIG. 26.

In a further aspect of the invention, the calculated results may be communicated as a graphical output 196, such as is illustrated in FIG. 27. The graphical output 196 may be accessed by pressing a graph report button 198 on the report output dialog box 196. The graphical output 196 is useful to further illustrate to the physician and the patient the changes in the calculated risk value over time, and in relation to changes in the cholesterol levels. The graphical output 196 is also useful as a further tool in enabling a patient to understand the relationship between their health habits and the associated risk factor, and in encouraging the patient to participate in their own medical decision making.

From the above description it should be apparent that the present system enables a physician or medical facility to track its progress or success in addressing chronic diseases. In particular, the present system provides a measurable output for gauging the effectiveness of the treatment of its patients. Further, the present system facilitates the implementation of effective patient treatment in that calculated outputs provide an immediate indicator for a physician to determine a patient's health risk level, and for tracking the progress of individual patients. For example, the system can show a physician how medication is affecting a patient's condition and can be used to track results of a particular treatment, as well as provide a means for comparing different treatments for effectiveness. The system additionally, operates to save time for the physician in that lab results may be directly input from lab equipment and therefore may be readily processed by the present system, thereby saving time and avoiding operator input errors. Also, the system facilitates performance of calculations which may either consume a significant cumulative amount of the physician's time, or which the physician may not perform due to either the complexity of the calculation or the time requirement for the calculation.

It should further be noted that the health risk calculations developed by one user of the system are transferable to another user of the system. Accordingly, one physician using the present system may share, or transfer to another physician using the system, specific user defined field and record definitions. Similarly, a research facility developing methods for identifying relevant health risk factors and calculating health risks may readily transfer specific field and record definitions to physicians using the system, reducing the time required to disseminate current health care information.

While the method and system herein described constitute a preferred embodiment of this invention, it is to be understood that the invention is not limited to this precise method and system and that changes may be made without departing from the scope of the invention, which is defined in the appended claims.

What is claimed is:

1. A method of managing a patient encounter using an electronic medical records system for use within a medical office, the method comprising:
    a plurality of medical personnel collecting and storing individual patient medical information in specified fields on a computer;
    the computer providing a calculated field, said calculated field including a value calculated from information in at least one of said specified fields; and
    said calculated field providing an indication to a user of a health risk associated with said information in said at least one of said specified fields.

2. The method of claim 1 wherein said specified fields include information on demographics associated with a patient and information pertaining to a patient's condition at a particular patient encounter.

3. The method of claim 2 wherein said calculation includes both said information on demographics and said information pertinent to a patient's condition.

4. The method of claim 1 including providing a group of health risk values from two or more patient encounters and graphically displaying said health risk values.

5. The method of claim 4 including changing information in at least one of said specified fields, corresponding to a health change to be implemented by a patient, during a patient encounter, and said system changing said indication of said health risk value in response to said change of said information in said at least one field, and further including the step of displaying to said patient said changed indication of said health risk value at said patient encounter.

6. The method of claim 1 including changing information in at least one of said specified fields, corresponding to a health change to be implemented by a patient, during a patient encounter, and said system changing said indication of said health risk value in response to said change of said information in said at least one field, and further including the step of displaying to said patient said changed indication of said health risk value at said patient encounter.

7. The method of claim 1 wherein said calculated field corresponds to a health risk value for cardiovascular disease.

8. The method of claim 1 wherein said calculated field is determined by a health risk algorithm input by a user, and including the step of providing a dialog box for defining said health risk algorithm, and further including the step of accessing said dialog box and updating said health risk algorithm.

9. A method of assessing a patient's risk of a disease state for use within a medical office, the method comprising:
    a plurality of medical personnel collecting and storing individual patient medical diagnostic information on a computer;
    collecting and storing a medical algorithm that operates on said medical diagnostic information to generate a disease risk assessment;
    applying said algorithm to said diagnostic information to generate a risk assessment value; and
    generating a report to communicate said risk assessment value.

10. The method of claim 1 wherein said medical diagnostic information comprises patient demographic information and information pertaining to a patient's condition at a particular patient encounter.

11. The method of claim 10 wherein said calculation includes both said demographic information and said information pertaining to a patient's condition.

12. The method of claim 9 wherein said report comprises a graph of said risk assessment value.

13. The method of claim 9 wherein said report communicates risk assessment values from two or more patient encounters.

14. The method of claim 9 including the step of changing an input for said diagnostic information to provide a different risk assessment value, and communicating said different risk assessment value to a patient during a patient encounter.

15. The method of claim 9 wherein said algorithm is input by a user, and including the step of providing a dialog box for defining said algorithm, and further including the step of accessing said dialog box and updating said algorithm.

* * * * *